US009446205B2

(12) United States Patent
Norman et al.

(10) Patent No.: US 9,446,205 B2
(45) Date of Patent: Sep. 20, 2016

(54) ENTERAL FEEDING WARMING SYSTEM

(71) Applicant: Neonatal Product Group, Inc., Stilwell, KS (US)

(72) Inventors: Scott Norman, Stilwell, KS (US); Mark Petheram, Overland Park, KS (US); Anthony Hash, Olathe, KS (US)

(73) Assignee: Neonatal Product Group, Inc., Stilwell, KS (US)

( * ) Notice: Subject to any disclaimer, the term of this patent is extended or adjusted under 35 U.S.C. 154(b) by 182 days.

(21) Appl. No.: 14/262,430

(22) Filed: Apr. 25, 2014

(65) Prior Publication Data

US 2015/0305985 A1 Oct. 29, 2015

(51) Int. Cl.
*A61M 5/44* (2006.01)
*A61M 5/142* (2006.01)

(52) U.S. Cl.
CPC .............. *A61M 5/44* (2013.01); *A61M 5/142* (2013.01); *A61M 2205/3368* (2013.01); *A61M 2205/36* (2013.01); *A61M 2205/3653* (2013.01); *A61M 2240/00* (2013.01)

(58) Field of Classification Search
CPC .. A61M 5/44; A61M 2205/36; A61M 5/445; A61M 2205/3653; A61M 2210/1042; A61M 2240/00
USPC .................................................. 604/113, 114
See application file for complete search history.

(56) References Cited

U.S. PATENT DOCUMENTS

| | | | | |
|---|---|---|---|---|
| RE25,788 E | * | 6/1965 | Sheridan | A61M 25/0014 138/109 |
| 4,293,762 A | * | 10/1981 | Ogawa | 392/470 |
| 4,410,320 A | * | 10/1983 | Dykstra et al. | 604/270 |
| 4,532,414 A | * | 7/1985 | Shah et al. | 392/470 |
| 4,742,824 A | * | 5/1988 | Payton et al. | 128/207.18 |
| 5,875,282 A | * | 2/1999 | Jordan | A61M 5/44 165/170 |
| 6,146,359 A | * | 11/2000 | Carr | A61B 18/18 219/687 |
| 6,259,074 B1 | * | 7/2001 | Brunner et al. | 219/497 |
| 8,663,161 B2 | * | 3/2014 | Hyun et al. | 604/113 |
| 2007/0066963 A1 | * | 3/2007 | Tanghoj | 604/523 |
| 2012/0271271 A1 | * | 10/2012 | Hyun et al. | 604/500 |
| 2014/0207063 A1 | * | 7/2014 | Hyun | A61M 5/44 604/113 |
| 2014/0251866 A1 | * | 9/2014 | Smallman | B65D 1/34 206/557 |

* cited by examiner

*Primary Examiner* — Nathan R Price
*Assistant Examiner* — Weng Lee
(74) *Attorney, Agent, or Firm* — Hovey Williams LLP (57) ABSTRACT

An enteral feeding warming system for warming enteral feeding fluid and delivering the feeding fluid to an infant or other patient comprises a pump, a warming device, and an enteral feeding tube. The pump may be connected to an enteral feeding fluid source. The warming device includes a housing, a heating element, a heat spreader, a temperature sensor, a controller, a display, a number of user inputs, and a power source. The housing includes outer walls defining an interior chamber and a feeding tube channel separate from the interior chamber. The interior chamber retains the heating element, heat spreader, temperature sensor, and controller therein. The feeding tube channel includes a number of turns and straight sections for increasing an effective length of the feeding tube channel and receives an intermediate portion of the enteral feeding tube therein.

15 Claims, 7 Drawing Sheets

ENTERAL FEEDING WARMING SYSTEM

BACKGROUND

The present invention relates to enteral feeding warming systems for feeding infants and other patients.

Infants and other patients who cannot eat through their mouths must be fed nutritional fluid directly into their stomachs or intestines via an enteral feeding tube. Often, such fluids are expressed from a birth mother or prepared in advance and then refrigerated until needed. Thus, the fluids must be warmed prior to feeding. Conventional enteral feeding warming systems are used to warm enteral feeding fluid and to deliver the fluid into the infant's stomach or intestine. These systems include a pump, a warming device having a housing and a heating element, and an enteral feeding tube. The pump is connected to a fluid source and connected to a first end of the enteral feeding tube of the warming device. The housing of the warming device encloses the heating element and an intermediate portion of the enteral feeding tube. The second end of the enteral feeding tube is inserted into the infant's stomach or intestine through the infant's esophagus or through an incision in the infant's chest or abdomen.

The heating elements of these warming devices are often heated to a temperature of between 120° F. (49° C.) to 140° F. (60° C.). This high heat of 120° F. (49° C.) to 140° F. (60° C.) may negatively break down the nutrients in the fluid such that the infant receives reduced nutritional benefit from the fluid. The high heat may also introduce foreign particles from the plastic of the enteral feeding tube into the fluid.

SUMMARY

The present invention solves the above-described problems and provides a distinct advance in the art of enteral feeding warming systems. More particularly, the present invention provides an enteral feeding warming system that gradually warms nutritional fluid to a desired temperature and consistently maintains the desired temperature for enterally feeding the fluid to an infant or other patient.

Applicant has discovered that many patients, and infants in particular, experience feeding tolerance issues unless the refrigerated fluid is warmed to a temperature within a Thermal Neutral Zone (TNZ) between 90° F. (32° C.) and 100° F. (38° C.). Temperatures within this range are ideal for enzymes in the infant's digestive system to break down the nutrients in the fluid.

An embodiment of the present invention is an enteral feeding warming system that more effectively heats nutritional fluids to temperatures within the TNZ and then effectively and consistently maintains the fluids at these temperatures. The warming system broadly includes a pump, a warming device, and an enteral feeding tube.

The pump may be a low-flow electrically powered pump configured to be connected to a fluid bag or other fluid supply at its intake and configured to be connected to the enteral feeding tube at its output. The pump may also be a manually actuated device.

The warming device includes a housing, a heating element, a heat spreader, a temperature sensor, a controller, a display, a number of user inputs, and a power source. The housing includes first and second clamshell housing sections connected together by a hinge or other connecting mechanism. The first clamshell housing section includes outer walls defining an internal heating chamber. One of the outer walls also includes a slot that defines a feeding tube channel extending from one end of the housing to another end of the housing and including a number of turns for increasing its effective length. The turns include retention features such as primary and secondary portions curving in opposite directions in quick succession for retaining an intermediate portion of an enteral feeding tube in the feeding tube channel. The second clamshell housing section includes a mounting component for mounting the warming device onto a stand or other structure.

The heating element may be an electric silicon heating pad or other heating element positioned within the internal heating chamber for warming the fluid. The heat spreader is a metal plate or other heat distribution component and is positioned within the internal heating chamber near the heating element for evenly distributing heat from the heating element to the air in the internal chamber. The temperature sensor is a thermistor or other temperature gauge positioned within the heating chamber for sensing the temperature in the internal heating chamber. The controller includes a printed circuit board (PCB), a memory, and/or other electronic components for controlling the heating element and maintaining a desired temperature of the internal heating chamber. The display is a seven segment LCD display or other display and may include additional LED lights or other indicators for displaying information from the controller. The user inputs are positioned on an outside of the housing of the warming device and may include a power switch, reset button, or other user inputs for operating the warming device. The power source is a power cord or battery and supplies electric power to the heating element, the controller, and the display.

The enteral feeding tube may be any elongated hollow tube connectable to the pump's output at its first end and configured to be inserted into an infant's stomach or intestine at its second end. An intermediate portion of the enteral feeding tube may be inserted into the feeding tube channel of the first clamshell housing section for sending feeding fluid through the warming device.

In use, the enteral feeding warming system heats nutritional fluid to a temperature within the TNZ and delivers the warmed fluid to an infant's stomach or intestine. To prepare the enteral feeding warming system for feeding the infant, a user connects the intake of the pump to a fluid source and connects the first end of the enteral feeding tube to the output of the pump. The user then positions the intermediate portion of the enteral feeding tube in the feeding tube channel of the first clamshell housing section of the warming device. The user then closes the clamshell housing sections together so that the intermediate portion of the enteral feeding tube is enclosed within the feeding tube channel. The user then plugs in the power source and/or turns on the warming device so that the heating element begins to warm the air inside the internal heating chamber to a temperature between approximately 90° F. (32° C.) and 103° F. (39° C.). The display indicates the temperature of the air inside the internal heating chamber and indicates when the warming device is ready for heating the fluid.

Once the warming device is ready to heat the fluid, the user inserts the second end of the enteral feeding tube into the infant's stomach or intestine via the infant's esophagus or an incision in the infant's abdomen or chest. The user then activates or turns on the pump, which directs fluid from the fluid source into the warming device via the feeding tube. The heating element of the warming device then warms the fluid to a temperature within the TNZ as the fluid passes through the turns of the feeding tube channel of the warming device. The warmed fluid then continues through the feeding tube and into the infant's stomach or intestine.

The controller of the warming device maintains the temperature of the air in the internal heating chamber between approximately 90° F. (32° C.) and 103° F. (39° C.) when the warming device is on. When the controller determines via the temperature sensor that the air inside the internal heating chamber is above 103° F. (39° C.) or is above another predetermined temperature, the controller temporarily deactivates the heating element until the temperature of the air in the internal heating chamber has dropped to another predetermined temperature between 90° F. (32° C.) and 103° F. (39° C.).

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein.

The drawing figures do not limit the present invention to the specific embodiments disclosed and described herein. The drawings are not necessarily to scale, emphasis instead being placed upon dearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Figure 1:
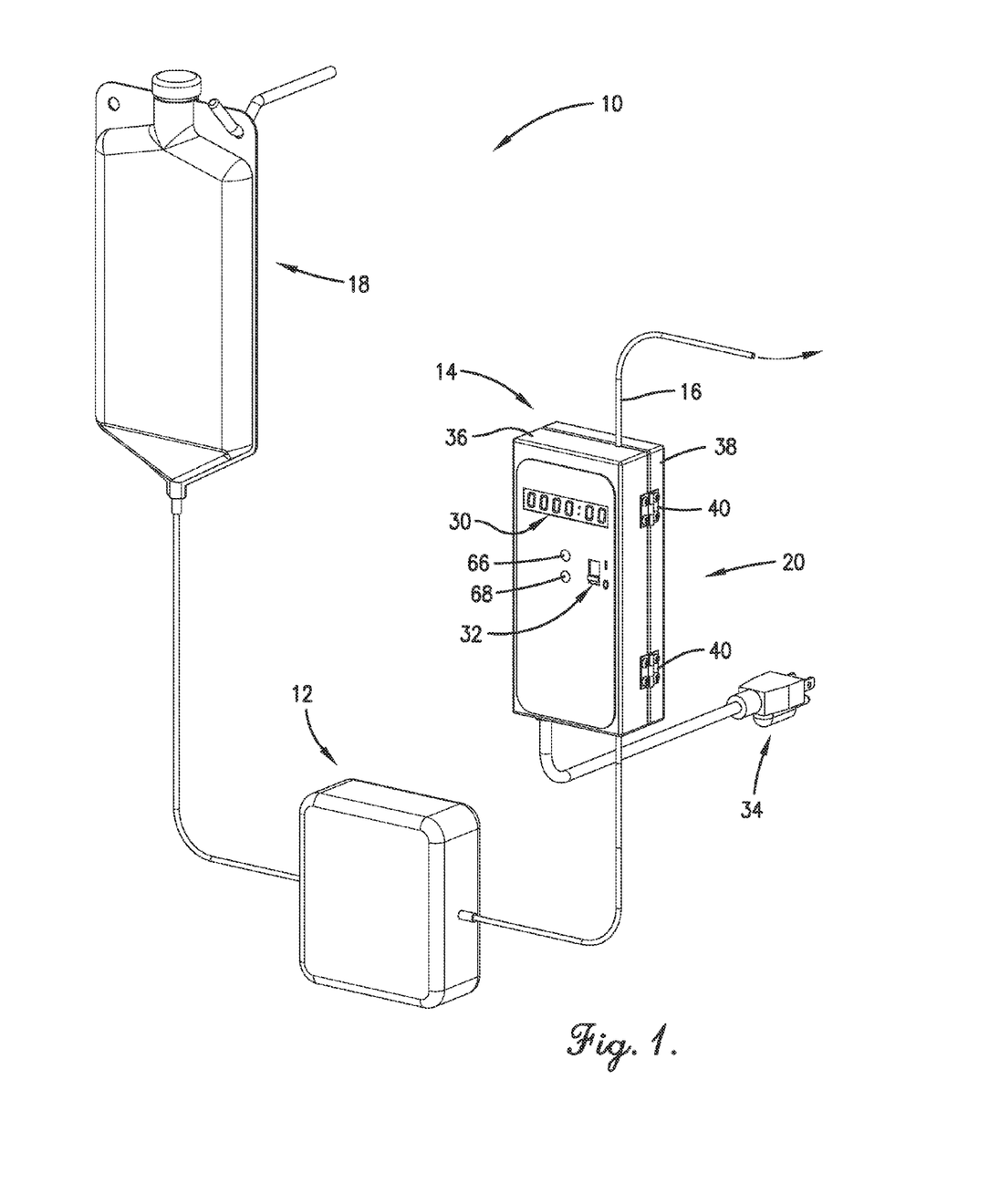
FIG. 1 is a perspective view of a enteral feeding warming system constructed in accordance with an embodiment of the present invention.

Turning now to the drawing figures, and particularly FIG. 1, an enteral feeding warming system 10 constructed in accordance with an embodiment of the invention is illustrated. The enteral feeding warming system 10 broadly comprises a pump 12, a warming device 14, and an enteral feeding tube 16.

The pump 12 draws enteral feeding fluid from a fluid bag or other fluid supply 18 and may be a low-flow centrifugal pump, diaphragm pump, or other type of electrically powered pump. The pump may also be a manually actuated device. The pump 12 is connected to the fluid supply 18 at its intake and connected to an enteral feeding tube of the warming device 14 at its output.

The warming device 14 warms the enteral feeding fluid to a temperature within a Thermal Neutral Zone (TNZ) and includes a housing 20, a heating element 22, a heat spreader 24, a temperature sensor 26, a controller 28, a display 30, one or more user inputs 32, and a power source 34.

Figure 2:
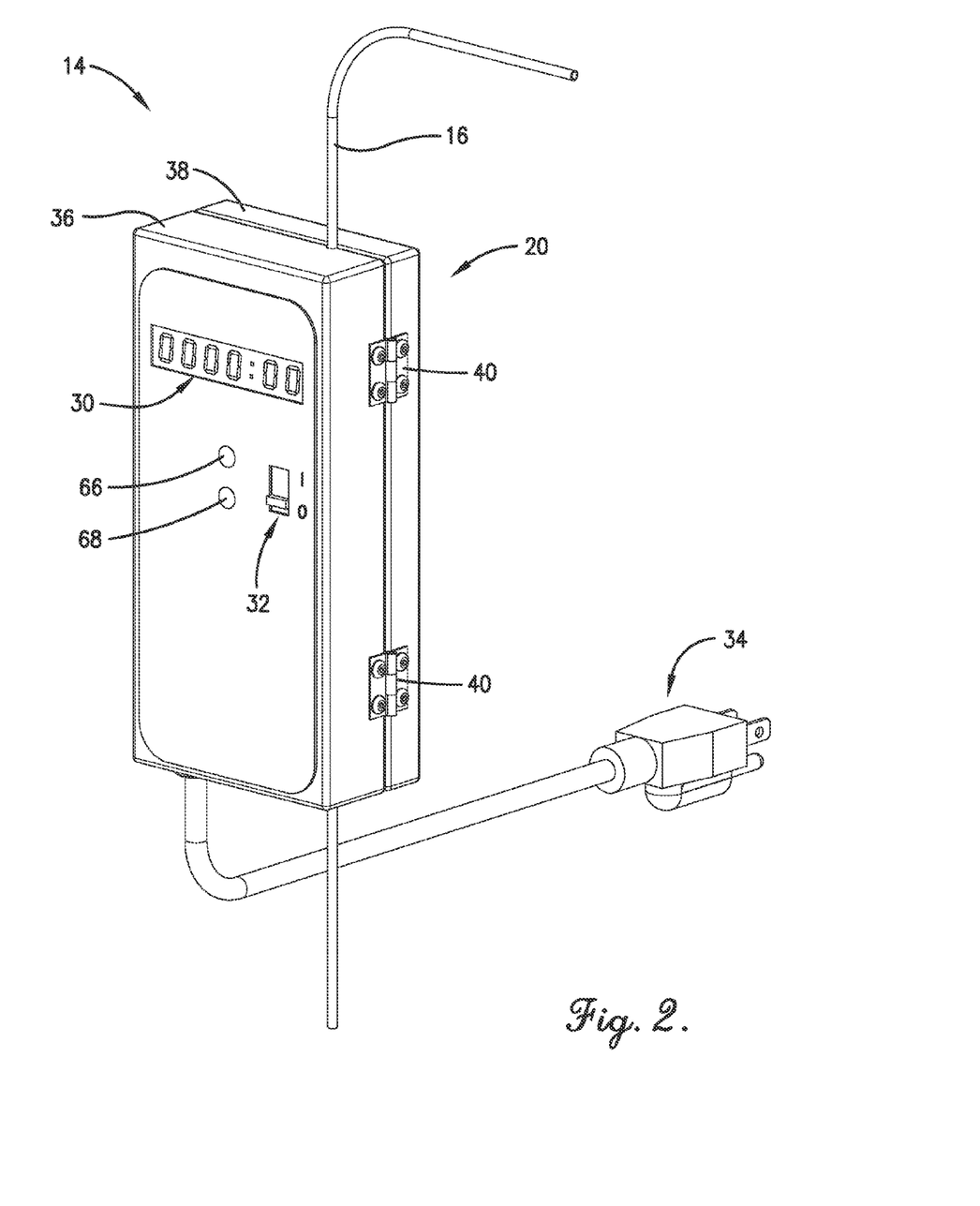
FIG. 2 is an enlarged perspective view of the warming device of FIG. 1.

The housing 20 encloses and protects the components of the warming device 14 and is formed of water resistant plastic or other heat insulating material, as shown in FIG. 2. The housing is approximately 7 inches long, 3.25 inches wide, and 2 inches deep and includes first and second clamshell housing sections 36, 38, a set of hinges 40, and a set of magnets 42. The housing 20 together with the above heating components is approximately 22.5 ounces or lighter.

Figure 6:
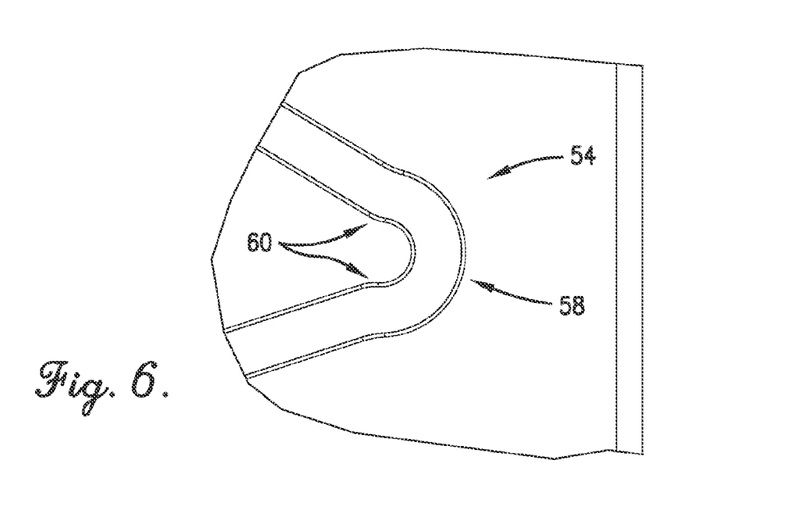
FIG. 6 is an enlarged partial elevation view of the turns of the feeding tube channel of the warming device of FIG. 1.

The first clamshell housing section 36 includes outer walls 44 defining an interior chamber 46 and a slot 48 defining a feeding tube channel 50, as shown in FIGS. 4-7. The interior chamber 46 houses the heating element 22, the heat spreader 24, the temperature sensor 26, the controller 28, and the display 30 and includes a front opening 52. The front opening 52 allows the display 30 to be mounted to a front of the first clamshell housing section 36 and allows the display 30 to face outward so that the user can easily view the display 30. The feeding tube channel 50 retains the enteral feeding tube 16 within the warming device 14 and is formed into an outer surface of one of the outer walls 44 of the first clamshell housing section 36. The feeding tube channel 50 is approximately 0.06 inches (1.5 mm) to approximately 0.16 inches (4 mm) in diameter and is substantially rounded so as to contact approximately 180° around the outer surface of the enteral feeding tube 16. The feeding tube channel 50 includes five complete turns 54 and six complete straight sections 56 that weave laterally back and forth so that the effective length of the feeding tube channel 50 is approximately 12 inches to approximately 16 inches. The turns 54 include retention features such as a primary portion 58 and secondary portions 60 curving in opposite directions in quick succession for retaining the enteral feeding tube 16 in the feeding tube channel 50, as best shown in FIG. 6. The primary portion 58 curves in the direction of the turn. The secondary portions 60 are located on either end of the primary portion 58 and curve in the opposite direction of the turn.

Figure 3:
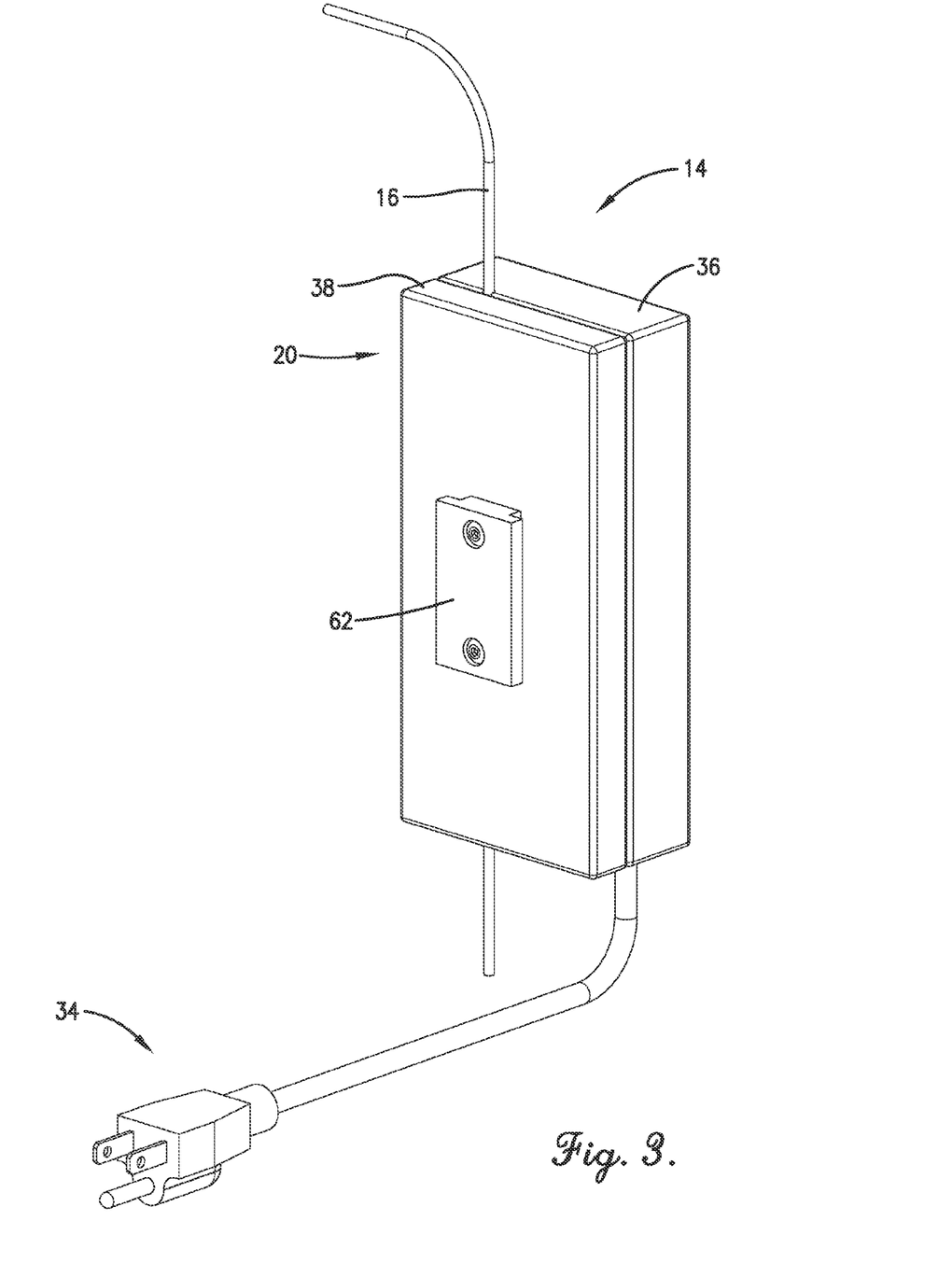
FIG. 3 is an enlarged rear perspective view of the warming device of FIG. 1.
Figure 4:
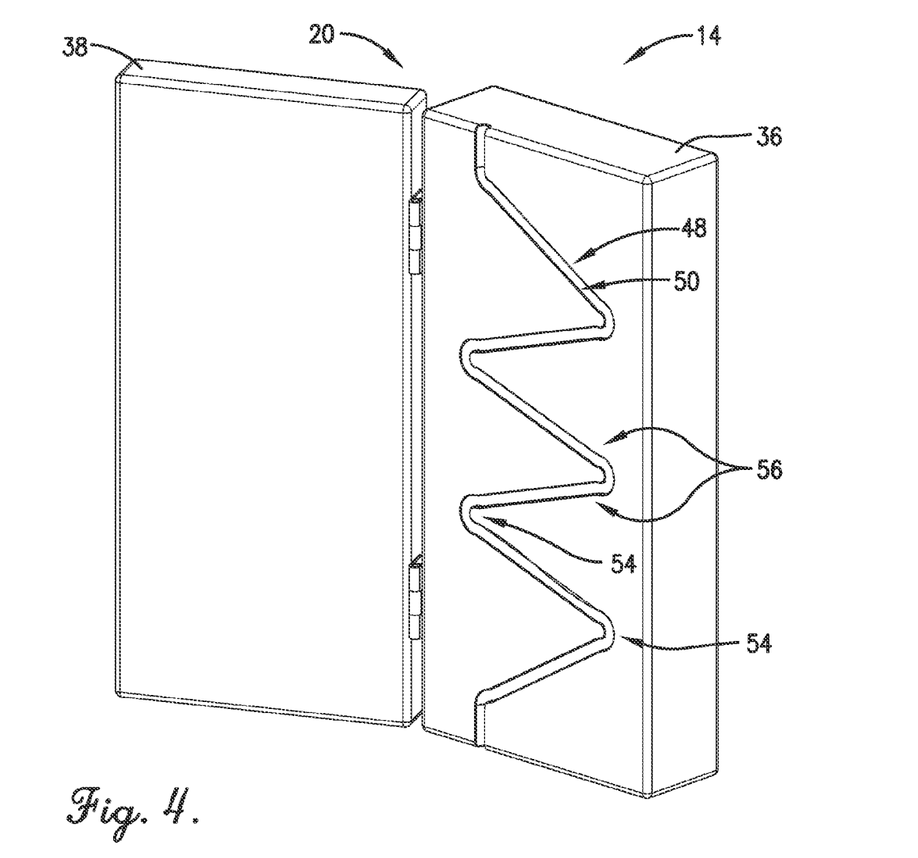
FIG. 4 is an enlarged perspective view of the warming device of FIG. 1 in which the clamshell housing sections are shifted to an open position.
Figure 5:
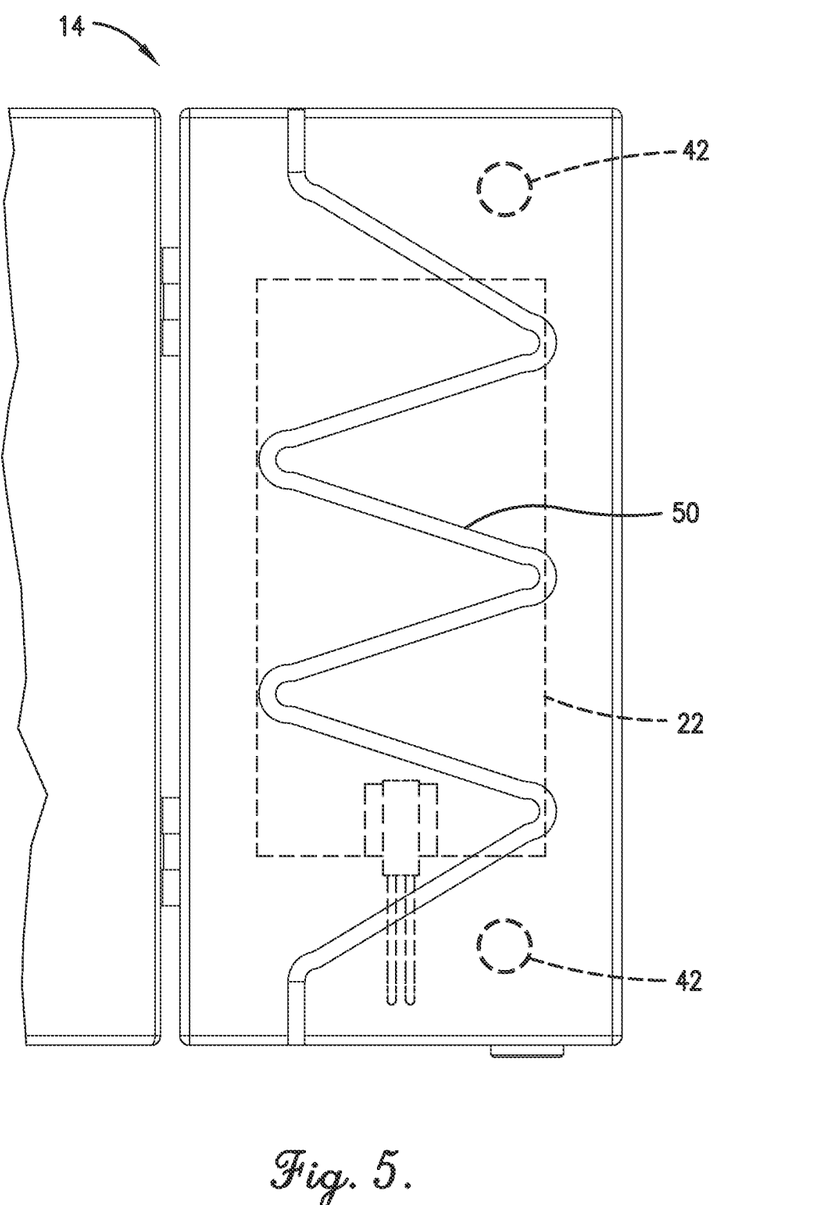
FIG. 5 is a partial elevation view of the warming device of FIG. 1.

The second clamshell housing section 38 encloses the enteral feeding tube 16 in the feeding tube channel 50 when the clamshell housing sections 36, 38 are in a closed position and includes a mounting component 62 positioned on its rear face, as shown in FIG. 3. The mounting component 62 may be a bracket, a hook and loop fastener, a hook, a clip, or any other mounting structure configured to removably attach the housing 20 to a stand, a multi-jointed arm, an incubator, a bed, or other structure.

The hinges 40 allow the clamshell housing sections 36, 38 to be pivoted with respect to each other between a closed position (FIGS. 2 and 3) and an open position (FIG. 4) and are connected to the clamshell housing sections 36, 38 via screws, bolts, rivets, or other fasteners.

Figure 7:
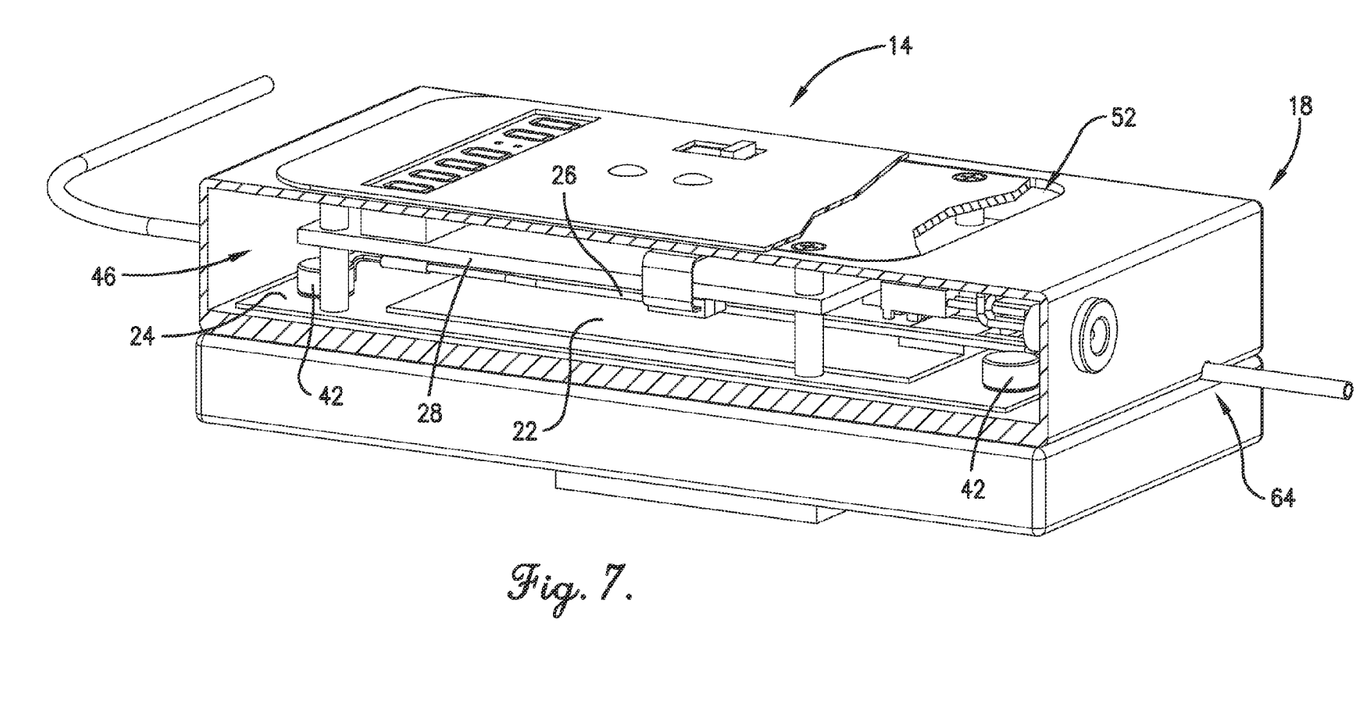
FIG. 7 is another enlarged perspective view of the warming device of FIG. 1.

The magnets 42 resistively retain the first and second clamshell housing sections 36, 38 in the closed position and are mounted in corresponding locations within or on the first and second clamshell housing sections 36, 38, as shown in FIG. 7. The magnets 42 are attached to the clamshell housing sections 36, 38 via adhesives or mounting bosses formed in the clamshell housing sections 36, 38.

The heating element 22 warms the air in the interior chamber 46 of the first clamshell housing section 36 and is a silicone heating pad, a resistive heater, or other heating element. The heating element 22 is mounted to a back wall of the first clamshell housing section 36 via adhesives or mounting bosses and is connected to the controller 28 and receives electrical power therefrom, as shown in FIG. 7.

The heat spreader 24 evenly spreads the heat generated by the heating element 22 and is a thin metal plate or other heat distribution component formed of aluminum, copper, or other suitable material. The heat spreader 24 is mounted to the back wall of the first clamshell housing section 36 behind the heating element 22 via adhesives or mounting bosses and substantially covers the back wall of the first clamshell housing section 36.

The temperature sensor 26 senses the temperature of the air in the interior chamber 46 of the first clamshell housing section 36 and may be a thermistor, thermocouple, a silicon bandgap temperature sensor, or any other temperature gauge. The temperature sensor 26 is mounted to a wall of the first clamshell housing section 36 in the interior chamber 46 via adhesives or mounting bosses and connected to the controller 28.

Figure 8:
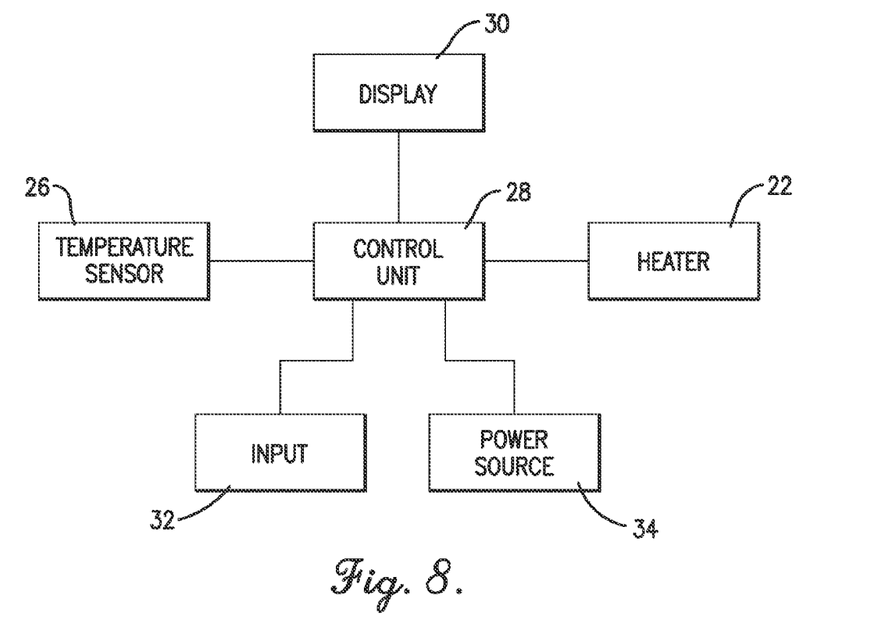
FIG. 8 is a schematic view of the electrical components of the warming device of FIG. 1.

The controller 28 regulates the air temperature in the interior chamber 46 and controls the heating element 22 and the display 30. The controller 28 includes a printed circuit board (PCB), a memory, and/or other electronic components and is mounted to a wall of the first clamshell housing section 36 in the interior chamber 46 via adhesives or mounting bosses. The controller 28 is connected to the heating element 22, the temperature sensor 26, the display 30, the user inputs 32, and the power source 34, as shown in FIG. 8.

The controller 28 may implement aspects of the present invention with one or more computer programs stored in or on computer-readable medium residing on or accessible by the controller 28. Each computer program preferably comprises an ordered listing of executable instructions for implementing logical functions in the controller 28. Each computer program can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can store the program for use by or in connection with the instruction execution system, apparatus, or device. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The display 30 provides a visual indication of the temperature of the interior chamber 46 and other information and may be a seven segment LCD display, an analog display, a touch screen, or any other display. The display 30 may include additional LED lights 64, 66 and other indicators for providing additional information to the user. The display 30 is mounted in the front opening 52 of the first clamshell housing section 36 facing outward from the housing 20 and connected to the controller, as shown in FIG. 2.

The user inputs 32 allow the user to turn the warming device 14 on and off, to program the warming device 14, to reset the warming device 14, and to perform other functions and may include switches, buttons, dials, and other user inputs. The user inputs 32 may comprise a power button or power switch, a reset button, a calibration button, a temperature unit toggle button, and other inputs.

The power source 34 supplies electrical power to the heating element 22, temperature sensor 26, the controller 28, and the display 30 and includes a power cord for connecting to a 100 volt or 240 volt, 60 W/hr or 100 W/hr, 50/60 Hz outlet, or any other power outlet.

The enteral feeding tube 16 carries the fluid from the pump 12, through the feeding tube channel 50, and into the infant's stomach or intestine. The enteral feeding tube 16 is plastic or any other suitable material and includes an intermediate portion 64 for inserting into the warming device 14, as shown in FIG. 7. The enteral feeding tube 16 has an outer diameter of approximately 006 inches (1.5 mm) to approximately 0.16 inches (4 mm) and an inside diameter sufficiently large to accommodate a fluid flow rate of approximately 0.25 ml/min to approximately 1 ml/min.

Operation of the enteral feeding warming system 10 will now be described in more detail. First, a user connects the intake of the pump 12 to the fluid supply 18 and the first end of the enteral feeding tube 16 to the output of the pump 12. Alternatively, the user may connect the fluid supply 18 to the first end of the enteral feeding tube 16 if the fluid supply 18 is gravity fed. The user then shifts the clamshell housing sections 36, 38 of the warming device 14 to an open position. The user may need to apply a small prying force to the clamshell housing sections 36, 38 to separate the magnets 42 from each other. The user then inserts the intermediate portion 64 of the enteral feeding tube 16 into the feeding tube channel 50 so that the enteral feeding tube 16 lays flush with the rear face of the first clamshell housing section 36. The user may need to push small sections of the enteral feeding tube 16 into the primary and secondary portions 56, 58 of the turns 54 of the feeding tube channel 50 to ensure that the enteral feeding tube 16 is fully seated in the feeding tube channel 50. The user then shifts the clamshell housing sections 36, 38 to a closed position so that the intermediate portion 64 of the enteral feeding tube 16 is fully enclosed in the housing 20 of the warming device 14. The user then mounts the warming device 14 on a stand or other structure via the mounting component 62 or places the warming device 14 in the infant's incubator so that the display 30 is easily readable.

The user then turns on the warming device 14 by plugging in the power source 34 of the warming device 14 or pressing the power button of the user inputs 32. The controller 28 will initiate a power on sequence in which it instructs the display 30 to display an indication that the warming device 14 is fully operational. If the controller 28 or other components of the warming device 14 are not fully operational, the controller 28 may generate an error message and instruct the display 30 to display the error message indicating to the user that the warming device 14 or a component of the warming device 14 should be serviced. The controller 28 will activate the heating element 22 if the warming device 14 is fully functional so that the heating element 22 begins to warm the air in the interior chamber 46 of the first clamshell housing section 36 of the warming device.

The controller 28 monitors the temperature of the air in the interior chamber 46 of the first clamshell housing section 36 by sending a signal to the temperature sensor 26, which returns a signal representative of the temperature to the controller 28. The controller 28 instructs the display 30 to display the temperature of the air in the interior chamber 46. If the air temperature is less than a predetermined lower threshold temperature, such as 90° F. (32° C.), the heating element 22 continues to warm the air in the interior chamber 46 and the controller 28 instructs the display 30 to indicate via the LED light 66 that the warming device 14 is not ready to warm the enteral feeding fluid. Warming the air temperature from room temperature to the predetermined lower threshold temperature should take approximately 2 to 3 minutes.

The controller 28 instructs the display 30 to indicate via the other LED light 68 that the warming device 14 is ready to warm the enteral feeding fluid when the air temperature in the interior chamber 46 reaches the predetermined lower threshold temperature. The user may then insert the second end of the enteral feeding tube 16 into the infant's stomach or intestine and may then turn on or activate the pump 12. The pump 12 draws the feeding fluid from the fluid supply 18 and forces it through the enteral feeding tube 16 at a flow rate of approximately 0.25 ml/min to approximately 1 ml/min. The warm air in the interior chamber 46 of the first clamshell housing section 36 warms the enteral feeding fluid to a temperature within the TNZ as it passes through the intermediate portion 64 of the enteral feeding tube 16 in the feeding tube channel 50. The warmed enteral feeding fluid continues through the remainder of the enteral feeding tube 16 and is delivered into the infant's stomach or intestine via the second end of the enteral feeding tube 16.

At any time during operation, the controller 28 will temporarily deactivate the heating element 22 if the temperature of the air in the interior chamber 46 is greater than a predetermined upper threshold temperature, such as 103° F. (39° C.). The controller 28 will reactivate the heating element 22 when the air temperature drops to the predetermined lower threshold temperature or when the air temperature drops to an intermediate temperature as described below. This ensures that the temperature of the enteral feeding fluid exiting the intermediate portion 64 of the enteral feeding tube 16 is within the TNZ.

The controller 28 may maintain the temperature of the air in the interior chamber 46 at an intermediate temperature, such as 95° F. (35° C.), or within an intermediate temperature range, such as 93° F. (34° C.) to 97° F. (36° C.), by frequently activating and deactivating the heating element 22 when the air temperature reaches these temperatures. This allows the temperature of the air in the interior chamber 46, and hence the temperature of the enteral feeding fluid exiting the intermediate portion 64 of the enteral feeding tube 16 and being delivered into the infant's stomach or intestine, to remain relatively constant during operation instead of rising and falling between the upper and lower threshold temperatures of the TNZ.

It will be understood that one or more of the above-described steps may be performed in a different order than described or simultaneously. For example, the warming device 14 may be turned on before the first end of the enteral feeding tube 16 is connected to the output of the pump 12. As another example, the heating element 22 may begin warming the air in the interior chamber 46 of the first clamshell housing section 36 at the same time that the user inserts the intermediate portion 64 of the enteral feeding tube 16 into the interior chamber 46.

The above-described enteral feeding warming system 10 provides several advantages over conventional systems. For example, the warming device 14 gradually warms the enteral feeding fluid to a temperature in the TNZ. The turns 54 and straight sections 56 of the feeding tube channel 50 of the warming device 14 increase the effective length of the feeding tube channel 50, which allows the enteral feeding fluid to be exposed to the heat of the warm air for an extended duration of time. The extended exposure allows the warming device 14 to warm the enteral feeding fluid to a temperature within the TNZ without using high heat to warm the enteral feeding fluid. This prevents the nutrients in the enteral feeding fluid from breaking down and prevents the enteral feeding tube 16 from introducing foreign particles into the fluid. The feeding tube channel 50 being formed on an outside of the first clamshell housing section 36 allows the enteral feeding tube 16 to be inserted into and removed from the warming device 14 without exposing the heating element 22 and the controller 28. The primary and secondary portions 56, 58 of the turns 54 of the feeding tube channel 50 prevent the enteral feeding tube 16 from slipping out of the feeding tube channel 50. The magnets 42 of the first and second clamshell housing sections 36, 38 ensure that the enteral feeding tube 16 is completely enclosed within the warming device 14 so that minimal heat is lost to ambient air. Moreover, the mounting component 62 allows the warming device 14 to be positioned at a convenient height and location so that the display 30 is easily readable and so that the second end of the enteral feeding tube 16 may be easily inserted into the infant's stomach or intestine. The warming device 14 may also be mounted onto or placed inside an incubator for reducing the risk of the warming device 14 becoming dislodged or disconnected during use. The heat spreader 24 also allows the interior chamber 46 of the warming device 14 to be cleaned easily and minimizes the buildup of dirt and debris inside the interior chamber 46.

Figure 9:
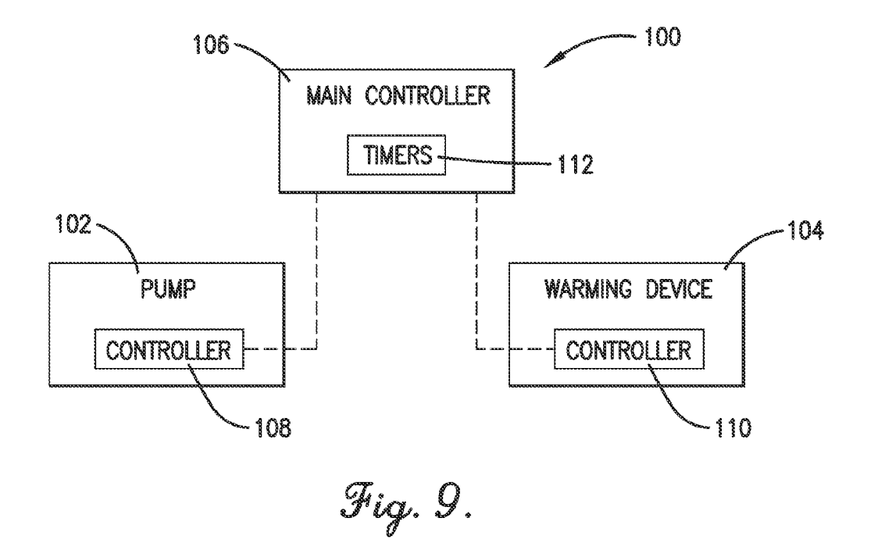
FIG. 9 is a schematic view of another enteral feeding warming system for use with another embodiment of the invention.

Turning now to FIG. 9, an enteral feeding warming system 100 constructed in accordance with another embodiment of the invention is illustrated. The enteral feeding warming system 100 comprises a pump 102, a warming device 104, a main controller 106, and an enteral feeding tube.

The pump 102 is substantially similar to the pump described above except the pump 102 includes a controller 108 that controls the pump 102 and communicates with the main controller 106. The controller 108 includes electronic components similar to the controller described above and may include a transceiver for sending wireless signals to and receiving wireless signals from the main controller 106.

The warming device 104 is substantially similar to the warming device described above except the warming device 104 includes a controller 110 that controls the warming device 104 and communicates with the main controller 106. The controller 110 includes electrical components similar to the controllers described above and may include a transceiver for sending wireless signals to and receiving wireless signals from the main controller 106.

The main controller 106 coordinates operation of the pump 102 and the warming device 104 and is substantially similar to the controllers described above except the controller 106 includes one or more timers 112, a transceiver, and other electronic components. The timers 112 trigger controller operations based on calculated or pre-determined time constraints and may be quartz timers or simulated timers.

The enteral feeding system 100 operates substantially similar to the above-described enteral feeding system except the main controller 106 coordinates operation of the pump 102 and the warming device 104 via the pump controller 108 and the warming device controller 110 to regulate fluid flow rate and fluid temperature. For example, to increase the fluid flow rate of the fluid being fed to the infant, the main controller 106 transmits a signal representing an instruction to increase pump speed to the pump controller 108. The pump controller 108 receives the signal via its transceiver and instructs the pump 102 to increase its speed, thereby increasing the fluid flow rate of the fluid being fed to the infant. The main controller 106 also transmits a signal representing an instruction to increase a temperature of the warming device 104 to the warming device controller 110 to compensate for the reduction of warming time of the fluid passing through the warming device 104. The warming device controller 110 receives the signal via its transceiver and instructs the heating element of the warming device 104 to increase the temperature within the internal chamber of the warming device 104. The increased temperature warms the faster-moving fluid passing through the warming device 104 to a temperature substantially the same as the temperature reached by the slower-moving fluid. To decrease the fluid flow rate of the fluid being fed to the infant, the main controller 106 instructs the pump controller 108 to decrease the pump speed, thereby decreasing the fluid flow rate. The main controller 106 also instructs the warming device 104 to decrease its internal temperature to compensate for the increase in warming time of the fluid passing through the warming device 104.

The controllers 106, 108, and 110 may perform the above operations at Limed intervals using the timer 112. For example, the main controller 106 may instruct the warming device 104 to increase or decrease its internal temperature and simultaneously start the timer 112 before activating the pump 102 so that the heating element of the warming device 104 has time to warm up. Once the timer 112 reaches a predetermined time interval such as ten seconds to three minutes, the timer 112 may trigger the main controller 106 to instruct the pump 102 to increase or decrease its fluid flow rate.

It will be understood that one or more of the above-described steps may be performed in a different order than described or simultaneously.

The above-described enteral feeding warming system 100 provides several advantages over conventional systems. For example, the enteral feeding warming system 100 may increase and decrease the fluid flow rate and the temperature of the fluid without increasing or decreasing the other. The enteral feeding warming system 100 may also fine-tune the fluid flow rate and the temperature of the fluid for each infant's medical needs. In addition, timing of the above operations may be modified as needed via the timer 112 of the main controller 106.

Although the invention has been described with reference to the embodiments illustrated in the attached drawing figures, it is noted that equivalents may be employed and substitutions made herein without departing from the scope of the invention as recited in the claims.

Having thus desribed various embodiments of the invention, what is claimed as new and desired to protected by Letters Patent includes the following:

1. An enteral feeding warming device comprising:
a housing having first and second mating clamshell housing sections connected by a hinge mechanism, the first housing section having exterior walls defining an internal heating chamber, each housing section having at least one complementary magnet for releasably retaining the housing sections in a closed configuration;
a channel formed in one of the exterior walls of the first housing section, the channel having a straight entry section, a first partial turn, six complete straight sections and five complete turns alternating with each other to form a back-and-forth pattern, a second partial turn, and a straight exit section in that order, the straight entry section and the straight exit section each being shorter than the complete straight sections, the complete turns each including a primary region curving in a first direction and two secondary regions curving in a second direction opposite the first direction, the channel having a substantially semi-circular cross section with a diameter of between 0.06 inches and 0.16 inches and an effective length of between 12 inches and 16 inches for receiving an enteral feeding tube having an outer surface, a first end for receiving feeding fluid from a storage device, and a second end for administering the feeding fluid to a patient at a fluid flow rate of between approximately 0.25 milliliters per minute and approximately 1 milliliter per minute, the channel being configured to contact the enteral feeding tube at least 180 degrees around the outer surface of the enteral feeding tube without an air gap between the channel and the enteral feeding tube so that heat is transferred directly from the warming device to the enteral feeding tube, the primary region and the two secondary being cooperatively configured to retain the enteral feeding tube in the channel;
a heating element positioned within the internal heating chamber of the first housing section and configured to heat the channel for warming the feeding fluid in the enteral feeding tube;
a controller for controlling operation of the heating element such that the feeding fluid administered from the second end of the feeding tube is warmed to a temperature between 90 degrees and 103 degrees Fahrenheit; and
a heat spreader positioned within the internal heating chamber of the first housing section for uniformly spreading heat from the heating element so that the heating element does not warm air in the housing to a temperature greater than 103 degrees Fahrenheit so that the fluid is gradually warmed through the entire length of the channel.

2. The enteral feeding warming device of claim 1, wherein the controller is configured to instruct the heating element to continuously warm the air in the interior chamber if the air in the interior chamber has a temperature of less than 90 degrees Fahrenheit.

3. The enteral feeding warming device of claim 1, further comprising a temperature sensor for sensing an internal temperature of the enteral feeding warming device, the controller being configured to control the operation of the heater based on the temperature sensed by the temperature sensor.

4. The enteral feeding warming device of claim 3, wherein the temperature sensor is a thermistor.

5. The enteral feeding warming device of claim 3, further comprising a display configured to indicate the internal temperature of the enteral feeding warming device.

6. The enteral feeding warming device of claim 5, wherein the display is further configured to indicate information related to operation of the enteral feeding warming device, the information including: a power status, a heating status, a ready status, an error, a warning, a time, a time counter, and a user instruction.

7. The enteral feeding warming device of claim 5, wherein the display is further configured to indicate when the enteral feeding warming device is ready to begin warming the feeding fluid for being administered to the patient.

8. The enteral feeding warming device of claim 1, further comprising a power switch for turning on and turning off the enteral feeding warming device.

9. The enteral feeding warming device of claim 1, wherein the housing further comprises a mount for mounting the enteral feeding warming device on a support.

10. The enteral feeding warming device of claim 1, wherein the heating element is a silicone heating pad.

11. An enteral feeding warming system comprising:
an electric pump configured to pump feeding fluid from a storage source at a flow rate of between approximately 0.25 millimeters per minute and approximately 1 millimeter per minute;
an enteral feeding warming device comprising:
a housing having:
first and second mating clamshell housing sections connected by a hinge mechanism, the first housing section having exterior walls defining an internal heating chamber, each housing section having at least one complementary magnet for releasably retaining the housing sections in a closed configuration; and
a mount connected to one of the housing sections for mounting the enteral feeding warming device on a support;
a channel formed in one of the exterior walls of the first housing section, the channel having a straight entry section, a first partial turn, six complete straight sections and five complete turns alternating with each other to form a back-and-forth pattern, a second partial turn, and a straight exit section in that order, the straight entry section and the straight exit section each being shorter than the complete straight sections, the complete turns each including a primary region curving in a first direction and two secondary regions curving in a second direction opposite the first direction, the channel having a substantially semi-circular cross section with a diameter of between 0.06 inches and 0.16 inches and an effective length of between 12 inches and 16 inches for receiving an enteral feeding tube having an outer surface, a first end for receiving feeding fluid from a storage device, and a second end for administering the feeding fluid to a patient at a fluid flow rate of between approximately 0.25 milliliters per minute and approximately 1 milliliter per minute, the channel being configured to contact the enteral feeding tube at least 180 degrees around the outer surface of the enteral feeding tube without an air gap between the channel and the enteral feeding tube so that heat is transferred directly from the warming device to the enteral feeding tube, the primary region and the two secondary regions being cooperatively configured to retain the enteral feeding tube in the channel;
a silicone pad heating element positioned within the internal heating chamber of the first housing section and configured to heat the channel for warming the feeding fluid in the enteral feeding tube;
a thermistor temperature sensor for sensing an internal temperature of the enteral feeding warming device;
a power switch for turning on and turning off the enteral feeding warming device;
a controller for controlling operation of the heating element based on the temperature sensed by the temperature sensor such that the feeding fluid administered from the second end of the feeding tube is warmed to a temperature between 90 degrees and 103 degrees Fahrenheit;
a heat spreader positioned within the internal heating chamber of the first housing section for uniformly spreading heat from the heating element so that the heating element does not warm air in the housing to a temperature greater than 103 degrees Fahrenheit so that the fluid is gradually warmed through the entire length of the channel; and
a display configured to indicate the internal temperature of the enteral feeding warming device and information related to operation of the enteral feeding warming device, the information including: a power status, a heating status, a ready status, an error, a warning, a time, a time counter, and a user instruction.

12. The enteral feeding warming device of claim 1, wherein the housing is approximately 7 inches long, approximately 3.25 inches wide, and approximately 2 inches deep.

13. The enteral feeding warming device of claim 1, wherein the housing includes a back wall and the heating element is mounted to the back wall of the housing.

14. The enteral feeding warming device of claim 1, wherein the controller is configured to activate the heating element upon being powered on if the warming device is fully operational.

15. The enteral feeding warming device of claim 1, wherein the controller is configured to generate an error message upon being powered on if the warming device is not fully operational.

* * * * *